(12) United States Patent
Hatakeda et al.

(10) Patent No.: US 7,022,842 B2
(45) Date of Patent: Apr. 4, 2006

(54) PROCESS FOR SYNTHESIZING BETA-LACTAM

(75) Inventors: Kiyotaka Hatakeda, Miyagi (JP); Osamu Sato, Miyagi (JP); Mitsuhiro Kanakubo, Miyagi (JP); Yutaka Ikushima, Miyagi (JP); Kazuo Torii, Miyagi (JP)

(73) Assignee: National Institute of Advanced Industrial Science and Technology, Tokyo (JP)

( * ) Notice: Subject to any disclaimer, the term of this patent is extended or adjusted under 35 U.S.C. 154(b) by 172 days.

(21) Appl. No.: 10/450,450

(22) PCT Filed: Mar. 7, 2001

(86) PCT No.: PCT/JP01/01759

§ 371 (c)(1),
(2), (4) Date: Jun. 19, 2003

(87) PCT Pub. No.: WO02/50025

PCT Pub. Date: Jun. 27, 2002

(65) Prior Publication Data

US 2004/0030126 A1   Feb. 12, 2004

(30) Foreign Application Priority Data

Dec. 21, 2000   (JP) .............................. 2000-389408

(51) Int. Cl.
C07B 43/06   (2006.01)
C07D 205/08   (2006.01)

(52) U.S. Cl. ........................ 540/362; 540/200; 540/361

(58) Field of Classification Search ..................... None
See application file for complete search history.

(56) References Cited

U.S. PATENT DOCUMENTS 4,360,684 A * 11/1982 Cvetovich et al. .......... 549/291

FOREIGN PATENT DOCUMENTS

| EP | 51234 A1 * | 5/1982 |
|---|---|---|
| GB | 1268869 | 3/1972 |
| JP | 47-10715 | 3/1972 |
| JP | 49-9473 | 3/1974 |
| JP | 57-159758 | 10/1982 |
| JP | 58-144367 | 8/1983 |
| JP | 2002121183 A * | 4/2002 |

OTHER PUBLICATIONS

Shin-Jikken Kagaku Koza, Yuki Kagobutso no Gosei to Hanno (2), Maruzen, pp. 1197-1201.
J.C. Sheehan et al. Org. React., vol. 9, pp. 388-408 1957.
F.F. Blicke et al. J. Org. Chem., vol. 23, pp. 1102-1107 1958.
T. Kametani et al. Tetrahedron, vol. 36, pp. 715-719 1981.
C.W. Kim et al. Tetrahedron, vol. 31, pp. 2905-2906 1990.

* cited by examiner

*Primary Examiner*—Mark L. Berch
(74) *Attorney, Agent, or Firm*—Oblon, Spivak, McClelland, Maier & Neustadt, P.C.

(57) ABSTRACT

It is an object of the present invention to provide a method for synthesizing β-lactams and a method for manufacturing β-lactams in water of high-temperature and under high-pressure, and the present invention relates to a β-lactam synthesis method which is characterized in that β-lactams are synthesized by reacting β-amino acids in water at high-temperature and under high-pressure, this method being further characterized in that β-lactams are synthesized at a high speed by cyclizing β-amino acids in water at high-temperature and under high-pressure in which the temperature range is 200° C. or higher and the pressure range is 10 MPa or greater, and the present invention also relates to a method for manufacturing β-lactams which is characterized in that β-lactams are synthesized by reacting β-amino acids in water at high-temperature and under high-pressure, and are then separated and purified using a column separation medium.

10 Claims, 2 Drawing Sheets

PROCESS FOR SYNTHESIZING BETA-LACTAM

TECHNICAL FIELD

The present invention relates to a method for synthesizing β-lactams from β-amino acids under high temperature and high pressure, and more particularly relates to a method for synthesizing or manufacturing β-lactams by reacting β-amino acids in water at high-temperature and under high-pressure conditions.

The present invention makes it possible to synthesize or manufacture β-lactams under high temperature and high pressure, either continuously or in a batch type system, using β-amino acids as a reaction substrate without causing any organic solvent or catalyst to participate in the synthesis process; accordingly, the present invention provides a method that is suitable and useful as an industrial technique.

BACKGROUND ART

Cyclic amides of aminocarboxylic acids are called lactams; β-lactams have four rings. β-lactams are extremely important as the basic backbones of β-lactam antibiotics such as penicillin, cephalosporin and the like, and the synthesis of these compounds has long been widely studied.

Judging from the structure of β-lactams, synthesis by the cyclization of β-amino acids would appear to be most appropriate. If it were possible to cyclize β-amino acids directly by heating, this would be easy; however, it is known that β-amino acids themselves undergo 1,2- dissociation when heated, and do not form β-lactams (*Shin-Jikken Kagaku Koza, Yuki Kagobutsu no Gosei to Hanno* [Synthesis and reaction of organic compounds](2), Maruzen, p. 1197, (1978)). Methods in which β-amino acids are acylated and then subjected to direct heating cyclization (J. C. Sheehan and E. J. Corey, Org. React., 9, 393 (1957)), methods in which amino acid chlorides are treated with bases (F. F. Blicke and W. A. Gould, J. Org. Chem., 23, 1102 (1958)), methods in which β-amino acid esters are cyclized with a Grignard reagent (T. Kametani et. al., Tetrahedron, 37, 715 (1981)) and the like have long been reported. Meanwhile, in regard to methods for the cyclization of β-amino acids themselves, methods using ring-closing agents such as phosphorus trichloride, carbodiimide and the like have been studied. For example, β-lactams have been obtained by reacting free β-amino acids in acetonitrile using dichlorophosphoric acid and triethylamine (C. W. Kim and B. Y. Chung, Tetrahedron Lett., 31, 2905 (1990)). This method suffers from the following drawbacks: namely, highly toxic reagents and harmful organic solvents are used, and these compounds must be disposed of; furthermore, the reaction process is complicated and the reaction time is long. However, almost no method for the direct, simple and efficient cyclization of β-amino acids is known, and the development of such a method is currently awaited.

Under such conditions, the present inventors pursued various studies concerning methods for synthesizing β-lactams under high temperature and high pressure in light of the abovementioned prior art. In the process of this research, the inventors have discovered that β-lactams can be manufactured with good efficiency by reacting β-amino acids in water at high-temperature and under high-pressure conditions. Further research was conducted on the basis of this finding, and this research led to the perfection of the present invention.

SUMMARY OF THE INVENTION

The present invention provides a method for synthesizing β-lactams and a method for manufacturing β-lactams in water at high-temperature and under high-pressure.

The present invention relates to a β-lactam synthesis method which is characterized in that β-lactams are synthesized by reacting β-amino acids in water at high-temperature and under high-pressure conditions, this method being further characterized in that β-lactams are synthesized at a high speed by cyclizing β-amino acids in water at high-temperature and under high-pressure conditions in which the temperature range is 200° C. or higher and the pressure range is 10 MPa or greater; the present invention also relates to a method for manufacturing β-lactams which is characterized in that β-lactams are synthesized by reacting β-amino acids in water at high-temperature and under high-pressure conditions, and are then separated and purified using a column separation medium.

DISCLOSURE OF THE INVENTION

It is an object of the present invention to provide a novel β-lactam synthesis method in which for example β-propiolactam is synthesized by reacting β-alanine in water at high-temperature and under high-pressure conditions.

Further, it is an object of the present invention to provide a novel β-lactam synthesis method in continuous or batchwise manner by introducing β-amino acids into a reaction vessel under high-temperature high-pressure water conditions.

Furthermore, it is an object of the present invention to provide a method for manufacturing high-purity β-lactams which is characterized in that β-lactams are synthesized from β-amino acids by the abovementioned continuous synthesis method, and β-lactams are separated and purified by adding a column separation medium to the reaction solution thus obtained.

The present invention, which is used to solve the abovementioned problems, is constituted by the following technical means.

(1) A method for synthesizing β-lactam comprising reacting β-amino acids in water at high-temperature and under high-pressure conditions to synthesize β-lactam.

(2) The method for synthesizing β-lactam according to the abovementioned (1), wherein β-amino acid is reacted in water at high-temperature and under high-pressure conditions in which the temperature range is 200° C. or higher and the pressure range is 10 MPa or greater.

(3) The method for synthesizing β-lactam according to the abovementioned (1) or (2), wherein β-propiolactam is synthesized using β-alanine as a β-amino acid.

(4) The method for synthesizing β-lactam according to the abovementioned (1) or (2), wherein 4-methyl-2-azethidinone is synthesized using 3-amino-n-butyric acid as a β-amino acid.

(5) The method for synthesizing β-lactam according to one of the abovementioned (1) through (4), wherein β-amino acid is continuously introduced into a reaction vessel under high-temperature high-pressure water conditions, and is reacted therein.

(6) The method for synthesizing β-lactam according to one of the abovementioned (1) through (5), wherein β-amino acid is continuously introduced into a reaction vessel under high-temperature high-pressure water conditions, and is reacted at a high rate for a reaction time of 0.001 seconds to 10 minutes.

(7) A method for manufacturing β-lactams using β-amino acids as a reaction substrate under high-temperature high-pressure water conditions, comprising introducing a β-amino acid continuously into a reaction vessel under high-temperature high-pressure water conditions in which the temperature range is 200° C. or higher and the pressure range is 10 MPa or greater to react it in the vessel, cooling the reaction solution thus obtained, subjecting the reaction solution to a column separation medium to separate the reaction product, concentrating it, and then drying it to obtain a β-lactam.

(8) The method for manufacturing β-lactam according to the abovementioned (7), wherein an ion exchange resin is used as the column separation medium.

Next, the present invention will be described in greater detail.

Below, in order to facilitate the description of the present invention, a case in which, for example, β-propiolactam is synthesized from β-alanine as an amino acid by reacting the β-amino acid at a high temperature and under high pressure will be described in detail as an example. However, the present invention is not limited to such examples.

A method in which β-propiolactam is synthesized by introducing β-alanine into a reaction vessel under high-temperature high-pressure water conditions, and causing this β-alanine to pass through the reaction vessel at a high speed, may be indicated as a typical example of the synthesis method of the present invention that was developed through various experiments performed by the present inventors. The only raw-material reagents used in the synthesis method of the present invention are β-amino acids. In the present invention, high-temperature high-pressure water is used as a reaction medium or reaction solvent; there is no use of ring-closing agents, catalysts or organic solvents, or no particular need to use such reagents. Accordingly, if this method is used, no waste requiring treatment, such as waste reagents, waste organic solvents or waste catalysts that must be disposed of, are discharged. Furthermore, the unreacted β-amino acids and water that is used may be repeatedly used in the reaction of the present invention. Moreover, in the method of the present invention, useful products such as β-lactams and the like can be synthesized at a high speed; accordingly, it would appear that this method is most suitable as means for manufacturing such products. Furthermore, this reaction can also be accomplished using a batch system.

The β-lactam synthesis method of the present invention will be described in detail below.

There are cases in which five-ring γ-lactams or six-ring δ-lactams are produced by heating γ-amino acids or δ-amino acids. However, it is extremely difficult to synthesize β-lactams by a heat treatment form β-amino acids. Accordingly, even if β-alanine is heat-treated, β-propiolactam cannot be synthesized.

On the other hand, the present invention discovered that β-lactams can be synthesized simply by reacting β-amino acids in water at high-temperature and under high-pressure conditions so that these amino acids are cyclized. In this reaction, it appears that one molecule of the β-amino acid dissociates one molecule of water under high-temperature high-pressure water conditions, so that a cyclization reaction proceeds, thus producing one molecule of a β-lactm.

The β-amino acids that are used as raw materials in the present invention can be expressed by the following general formula (1) (Chemical Formula 1)

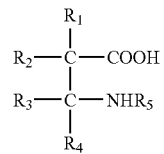

Chemical Formula 1

(In the above formula, $R_1$, $R_2$, $R_3$, $R_4$ and $R_5$ may be the same or different groups, and respectively indicate halogen, or alkyl groups, phenyl groups, phenylalkyl groups, aryl groups, cycloalkyl groups, alkenyl groups, arylalkyl groups with 1 to 15 carbon atoms, which may have substituent groups, or which may be unsubstituted. Furthermore, the substituent groups referred to here include halogen atoms, amino groups, amido groups, nitro groups, carbonyl groups, carboxyl groups, alkoxy groups, acetoxy groups, hydroxyl groups, mercapto groups, sulfone groups, sulfonyl groups, phosphoric acid groups, tosyl groups, ester groups, acyl groups, imido groups, phosphine groups, nitrile groups, alkylsilyl groups and the like.)

Concrete examples of such acids include β-alanine, 3-amino-n-butyric acid, β-anilino-β-phenylpropionic acid, N-isobutyryl-β-ethylamino-β-phenyl-α,α-dimethylpropionic acid, N-ethyl-β-aniline, 3-amino-4-methoxycarbonylbutyric acid and the like; however, the present invention is not limited to these acids.

The β-lactams of the present invention obtained from the β-amino acids expressed by general formula (1) used in the present invention can be expressed by the following general formula (2) (Chemical Formula 2)

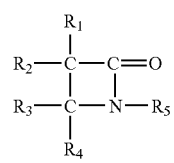

Chemical Formula 2

(In the above formula, $R_1$, $R_2$, $R_3$, $R_4$ and $R_5$ may be the same or different groups, and respectively indicate halogen, or alkyl groups, phenyl groups, phenylalkyl groups, aryl groups, cycloalkyl groups, alkenyl groups, arylalkyl groups with 1 to 15 carbon atoms, which may have substituent groups, or which may be unsubstituted. Furthermore, the substituent groups referred to here include halogen atoms, amino groups, amido groups, nitro groups, carbonyl groups, carboxyl groups, alkoxy groups, acetoxy groups, hydroxyl groups, mercapto groups, sulfone groups, sulfonyl groups, phosphoric acid groups, tosyl groups, ester groups, acyl groups, imido groups, phosphine groups, nitrile groups, alkylsilyl groups and the like.)

Examples of β-lactams that can be obtained using the present invention include β-propiolactam, 4-methyl-2-azethidinone, 1,4-diphenyl-2-azethidinone, 3,3-dimethyl-1-ethyl-4-phenyl-2-azethidinone and the like; however, the present invention is not limited to these β-lactams.

The reaction formula for the synthesis of β-propiolactam from β-alanine is shown in general formula 3 (Chemical Formula 3) as a concrete example of the β-lactam synthesis of the present invention.

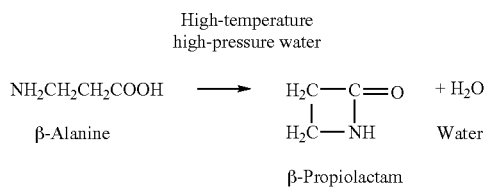

The temperature of the high-temperature high-pressure water used in the present invention can be controlled from the outside of the reaction vessel using a heater, molten salt or the like. Alternatively, the temperature can also be controlled by an internal heating system inside the reaction vessel. Furthermore, it would also be possible to perform a reaction by preparing high-temperature high-pressure water beforehand, and injecting this high-temperature high-pressure water into the reaction vessel from the outside using a water-feeding pump or the like. The reaction conditions may also be controlled by supplying two or more different types of high-temperature high-pressure water with different high-temperature high-pressure conditions to the reaction vessel. If the system used is a flow system, the pressure inside the reaction vessel may also be controlled by a pressure regulating valve. Furthermore, in regard to the reaction pressure in the case of a batch system, the self-generated pressure at the temperature used can be calculated. In addition, the pressure can be controlled by injecting another gas such as nitrogen gas or the like. It is generally sufficient if the pressure used is equal to or greater than the self-generated pressure at the temperature used.

Basically, the present invention can be achieved under high-temperature high-pressure water conditions in which the temperature is 200° C. or higher and the pressure is 10 MPa or greater. The present invention can be achieved even more desirably under high-temperature high-pressure water conditions in which the temperature is 300° C. or higher and the pressure is 15 MPa or greater. Furthermore, the present invention can be achieved most desirably if high-temperature high-pressure water conditions in which the temperature range is 350° C. or higher and the pressure range is 15 MPa to 40 MPa are selected. The optimal temperature conditions vary according to the treatment time; generally, however, a temperature range of 200° C. to 450° C. may be appropriately selected. Furthermore, appropriate temperature and pressure conditions may be used in accordance with the amount of treatment and the reaction apparatus. In the present invention, the reaction proceeds more readily at higher temperatures, and the reaction is somewhat accelerated by higher pressures.

For example, a high-temperature high-pressure reaction apparatus is used as the reaction apparatus. However, the present invention is not limited to such an apparatus; there are no restrictions on the type of apparatus used, as long as this apparatus is an apparatus that allows the setting of a reaction system under high-temperature high-pressure water conditions. Here, the flow type high-temperature high-pressure reaction apparatus or batch type reaction apparatus used in the present invention may be indicated as an example of an appropriate reaction apparatus. A commercially marketed autoclave may be appropriately used.

The reaction conditions vary according to the type and concentration of β-amino acid used, the reaction time, the flow velocity, the temperature of the high-temperature high-pressure water, and the pressure conditions.

In the present invention, a β-amino acid expressed by general formula (1) is used as the reaction substrate. β-Alanine may be cited as an example of such a β-amino acid. Any β-amino acid may be appropriately used in the present invention; all salts or esters of β-amino acids may also be appropriately used in the reaction. Alkali metal salts or alkaline earth metal salts of β-amino acids such as sodium salts, potassium salts, calcium salts and the like can all be used in the present invention. Furthermore, methyl esters, dimethyl esters, ethyl esters, propyl esters, phenyl esters and the like of β-amino acids can also all be appropriately used in the present invention. In the present invention, the β-amino acid used in the reaction is not limited to a single type of β-amino acid; the reaction will proceed appropriately even if a mixture of two or more types of β-amino acids is used.

In cases where a flow type apparatus is used, for example, the concentration of the β-amino acid that is introduced into the reaction vessel can be controlled by controlling the flow velocity of the high-temperature high-pressure water that is used as the carrier water and the flow velocity at which the β-amino acid that constitutes the reaction substrate is introduced into the reaction vessel. The β-amino acid can be introduced separately from the carrier water, or can be dissolved in the carrier water beforehand and supplied to the reaction. Ordinarily, a concentration range of 1 mM to 10 M may be selected as the concentration of the β-amino acid that is introduced into the reaction vessel. An appropriate concentration value between 2 mM and 5 M may be suitably selected, and an appropriate concentration value between 4 mM and 2 M is most suitably selected. However, this present invention is not limited to these concentration values. In the case of a bath method, it is sufficient to simply control the concentration of the starting β-amino acid. The concentration of the β-amino acid inside the control vessel varies according to the density of the high-temperature high-pressure water that participates in the reaction.

In the present invention, the reaction yield of the β-lactam can be controlled by adjusting the temperature and pressure of the reaction system, the reaction time and the concentration of the reaction substrate in accordance with the type of β-amino acid that is used.

In regard to the reaction system of the present invention, it is sufficient if the β-amino acid of the abovementioned reactions substrate is reacted in water at high-temperature and under high-pressure in which the temperature range is 200° C. or higher and the pressure range is 10 MPa or greater. In this case, for example, there is no particular need to use ring-closing agents that generally have a strong toxicity, such as phosphorus trichloride, ethyl dichlorophosphate, chlorinated methanesulfonic acid, 2,2-dipyridyl sulfide, triphenylphosphine, acetal chloride, thionyl chloride, acetic anhydride, triethylamine, dimethylaniline or the like, or to use organic solvents. Furthermore, there is no particular need to add water-soluble solvents such as metal ions, acids, bases or the like, solid catalysts such as metal-supported catalysts, solid acids, solid bases or the like, or enzymes.

Basically, the most important characterizing feature of the present invention is that β-lactams expressed by general formula (2) are synthesized by causing β-amino acids expressed by general formula (1) to be present in high-temperature high-pressure water, and simply reacting these β-amino acids under a high temperature and high pressure without using a ring-closing gent and without causing an organic solvent to participate in the reaction. If necessary, however, the reaction may be performed with the abovementioned ring-closing agents, organic solvents such as methanol, ethanol, ethylene glycol or the like, water-soluble catalysts such as metal ions, acids, bases or the like, ionic fluids, solid catalysts such as metal-supported catalysts, solid acids, solid bases or the like, and enzymes, added to the reaction system.

In the present invention, β-lactams are synthesized from β-amino acids in a short time, i.e., a reaction time of approximately 0.001 seconds to 10 minutes, using the abovementioned reaction system. For example, in cases where a flow type reaction apparatus is used, the reaction time can be controlled by controlling the reaction temperature, reaction pressure, flow velocity of the high-temperature high-pressure water, flow velocity at which the reaction substrate is introduced, size of the reaction vessel, length of the flow-through path in the reaction vessel and the like. Preferably, the reaction time is selected from a range of 0.01 seconds to 5 minutes; more preferably, the reaction time is selected from a range of 0.01 seconds to 3 minutes, and most preferably, the reaction time is selected from a range of 0.01 seconds to 1 minute. However, the present invention is not limited to these values.

As is shown in the examples that will be described later, the present inventors have confirmed using a high-performance liquid chromatography mass analysis apparatus (LC-MS apparatus) and a Fourier infrared spectroscopic photometer (FTIR apparatus) that β-lactams can be synthesized from β-amino acids in a short time (e.g., a reaction time of about 0.2 seconds) under high-temperature high-pressure water conditions. A separating column which uses silica gel supporting octadecyl groups (ODS) as a column separation medium (generally referred to as a reverse-phase silica gel column or ODS reverse-phase column) is used in this LC-MS apparatus. By using this LC-MS apparatus, it is possible to separate the raw-material β-amino acids and β-lactams, to identify these compounds individually, and to make an accurate determination of the contents of these compounds. Furthermore, the types of amino acid compounds and lactam compounds can be accurately identified by separating and purifying the continuously produced β-lactams using a separation medium such as an ion exchanger resin, reverse-phase column or the like, measuring the infrared absorption spectrum by means of an FTIR apparatus, and comparing this spectrum with that of, for example, a special grade reagent of high purity. Similarly, the β-amino acids and β-lactams can also be identified by NMR measurements, and the types and purity can be confirmed. For example, β-propiolactam with a concentration of 4.3 mM to 76.8 mM was successfully synthesized from β-alanine with a concentration of 60 mM to 200 mM at a temperature of 250° C. to 400° C., a pressure of 15 to 40 mPa and a reaction time of 0.013 seconds to 1.346 seconds using a flow-through type apparatus. Similarly, in the case of a batch system, a β-lactam with a concentration of 13.7 mM was synthesized from β-alanine at a temperature of 350° C., a pressure of 30 MPa and a reaction time of 40 seconds. It was confirmed by means of an LC-MS apparatus, an NMR measuring apparatus and an FTIR apparatus that as a result of these reactions, β-amino acids undergo a cyclization reaction in high-temperature high-pressure water, thus producing β-lactams.

The reaction yield of the β-lactams produced by the present invention fluctuates according to the reactions conditions such as temperature, pressure and the like, the type of β-amino acid used, the concentration of the β-amino acid, the configuration of the reaction apparatus, the size of the reaction vessel, the internal diameter and length of the reaction tube and the like. For example, the reaction yield in the case of β-propiolactam produced using a flow type apparatus ranges from 3.4% to 76.0%. Such β-propiolactam may alternatively be recovered as a mixture with the raw-material β-alanine or the like. Similarly, various types of β-lactams can be synthesized and recovered from various β-amino acids or mixtures of β-amino acids using the present invention. Following the reaction, β-lactams can be separated from the β-aminoacids and purified by using an ion exchange resin on the reaction solution thus obtained, e.g., a cation exchange resin or anion exchange resin, or both types of ion exchange resins used in combination. Furthermore, β-lactams can also be separated from each other, and β-amino acids similarly separated from each other in this way. Accordingly, β-lactams can be purified and concentrated according to type, so that high-purity products consisting of such β-lactams can be appropriately manufactured. At the same time, furthermore, the recovered β-amino acids that constitute the raw material substrate can be reused as raw materials. A common amino acid separation medium such as a reverse-phase silica gel (ODS supporting octadecyl groups or the like), cellite, alumina, powdered cellulose or the like can be utilized instead of an ion exchange resin.

In the present invention, for example, β-propiolactam is synthesized from β-alanine simply by reacting a β-amino acid with a specified concentration as a reaction substrate in high-temperature hot water under high-temperature high-pressure water conditions. In this case, if 3-amino-n-butyric acid is reacted instead of β-alanine, a cyclization reaction occurs so that 4-methylpropiolactam is synthesized. Furthermore, various β-lactams corresponding to respective β-amino acids can be continuously synthesized by continuously introducing these β-amino acids into a reaction vessel under high-temperature high-pressure water conditions.

Accordingly, the present invention makes it possible to synthesize β-lactams from β-amino acids in a short time by adjusting the reaction conditions, the type of β-amino acid that is used as a reaction substrate and the concentration of this β-amino acid in the abovementioned reaction system, so that the present invention is useful as a simple method for synthesizing or manufacturing novel β-lactams.

BEST MODE FOR CARRYING OUT THE INVENTION

Next, the present invention will be concretely described in terms of examples; however, the present invention is not limited in any way by the following examples.

EXAMPLE 1

Figure 1:
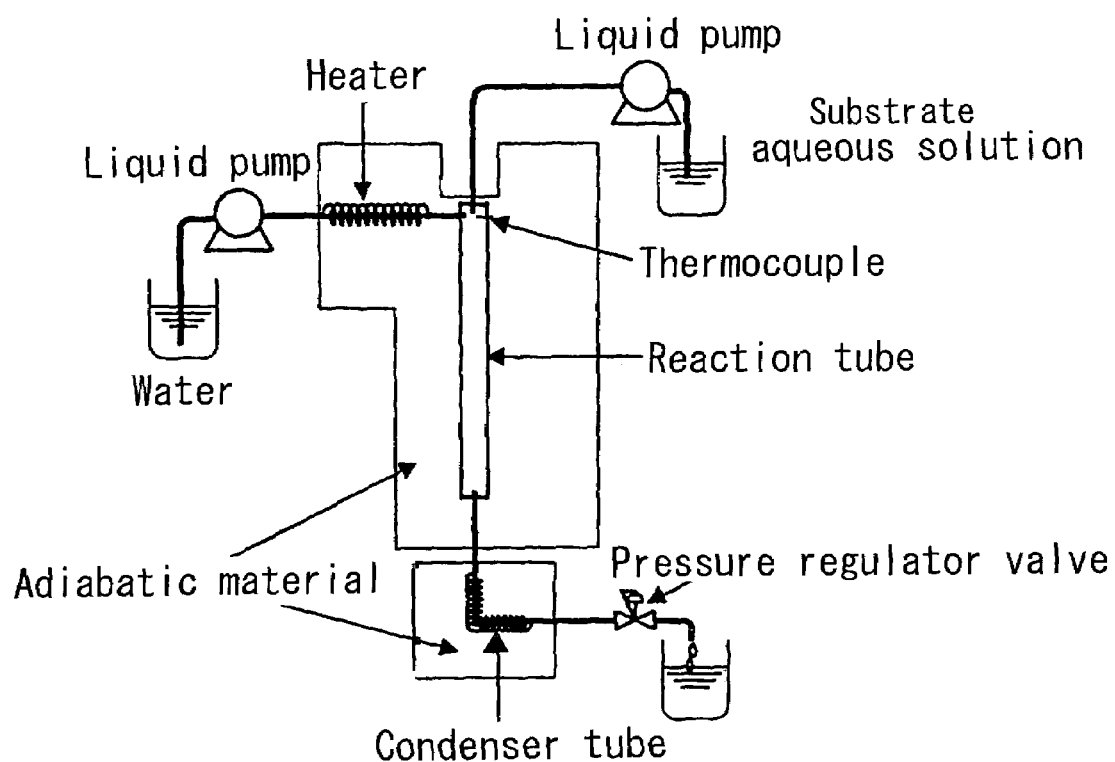
FIG. 1 shows a flow sheet for a flow type reaction apparatus equipped with two water-feeding pumps, which is used in the present invention.

The continuous synthesis of β-propiolactam by a cyclization reaction was attempted by reacting β-alanine (manufactured by Nakaraitekusu K.K.) under high-temperature high-pressure water conditions in which temperature 374° C., pressure 30 MPa and density 0.558 g/cm$^3$ using the continuous type reaction apparatus shown in FIG. 1.

The material of the reaction vessel was alloy C-276. The internal diameter of the reaction vessel was 0.65 mm and the length of the reaction vessel was 25 cm; accordingly, the volume of the reaction vessel was calculated as 0.083 cm$^3$. The respective prepared solutions that were introduced were injected by means of a high-pressure pump. The water used in the reaction was distilled water. The carrier water from which solute oxygen was driven out by bubbling with nitrogen gas was caused to flow through at a flow velocity of 10.3 ml/min. Similarly, using distilled water that had been subjected to a deoxygenation treatment, a substrate solution containing 0.5 M β-alanine was prepared, and this substrate solution was introduced into the reaction vessel at a flow velocity of 4.7 ml/min. The concentration of the β-alanine prior to introduction into the reaction vessel was 0.157 M. The reaction time was 0.185 seconds, and when the aqueous solution following the reaction was investigated using a high-performance liquid chromatography mass analysis apparatus, it was confirmed that β-propiolactam had been produced. The concentration of β-propiolactam in this solution was 76.8 mM and the reaction yield was 48.9%.

EXAMPLE 2

β-Propiolactam was continuously synthesized from β-alanine for 1 hour under exactly the same conditions as in Example 1. The reaction solution thus obtained was passed through a cation exchange resin (50W-X8 manufactured by Dow Chemical Co.) column, so that the raw-material β-alanine and the β-propiolactam that was produced were separated. After the solution containing β-propiolactam was concentrated, 4.6 of the product of the present invention was obtained. It was confirmed from FTIR absorption spectrum results and NMR measurement results that the product of the present invention thus obtained was high-purity β-propiolactam that contained almost no impurities.

EXAMPLE 3

The continuous synthesis of β-propiolactam from β-alanine was attempted by performing a reaction in the same manner as in Example 1. However, the reaction conditions were altered as shown below.
Altered Reaction Conditions
Reaction temperature: 400° C.
Reaction pressure: 15 MPa
High-temperature high-pressure water density: 0.064 g/cm$^3$
Carrier water flow velocity: 22 ml/min
Substrate solution flow velocity: 3 ml/min
The β-alanine concentration prior to introduction into the reaction vessel was 60 mM. The reaction time was 0.013 seconds, and when the aqueous solution following the reaction was investigated using a high-performance liquid chromatography mass analysis apparatus, it was confirmed that β-propiolactam had been produced. The concentration of β-propiolactam in the solution was 36.7 mM, and the reaction yield was 61.2%.

Comparative Example

The continuous synthesis of β-propiolactam from β-alanine by a cyclization reaction was attempted by performing a reaction in the same manner as in Example 1. However, the reaction conditions were altered as shown below.
Altered Reaction Conditions
Reaction temperature: 150° C.
Reaction pressure: 5 MPa
High-temperature high-pressure water density: 0.9196 g/cm$^3$
Carrier water flow velocity: 10 ml/min
Substrate solution flow velocity: 5 ml/min
The β-alanine concentration prior to introduction into the reaction vessel was 0.167 M. The reaction time was 0.305 seconds, and when the aqueous solution following the reaction was investigated using a high-performance liquid chromatography mass analysis apparatus, only β-alanine was detected; absolutely no β-propiolactam was produced.

EXAMPLE 4

The continuous synthesis of β-propiolactam from β-alanine was attempted by performing a reaction in the same manner as in Example 1. However, the reaction conditions were altered as shown below.
Altered Reaction Conditions
Reaction temperature: 250° C.
Reaction pressure: 15 MPa
High-temperature high-pressure water density: 0.811 g/cm$^3$
Carrier water flow velocity: 2 ml/min
Substrate solution flow velocity: 1 ml/min
The β-alanine concentration prior to introduction into the reaction vessel was 0.167 M. The reaction time was 1.34 seconds, and when the aqueous solution following the reaction was investigated using a high-performance liquid chromatography mass analysis apparatus, it was confirmed that β-propiolactam had been produced. The concentration of β-propiolactam in this solution was 4.3 mM, and the reaction yield was 2.6%.

EXAMPLE 5

The continuous synthesis of β-propiolactam from β-alanine was attempted by performing a reaction in the same manner as in Example 1. However, the reaction conditions were altered as shown below.
Altered Reaction Conditions
Reaction temperature: 300° C.
Reaction pressure: 40 MPa
High-temperature high-pressure water density: 0.765 g/cm$^3$
Carrier water flow velocity: 6 ml/min
Substrate solution flow velocity: 4 ml/min
The β-alanine concentration prior to introduction into the reaction vessel was 0.200 M. The reaction time was 0.381 seconds, and when the aqueous solution following the reaction was investigated using a high-performance liquid chromatography mass analysis apparatus, it was confirmed that β-propiolactam had been produced. The concentration of β-propiolactam in the solution was 37.2 mM, and the reaction yield was 18.6%.

EXAMPLE 6

The continuous synthesis of β-propiolactam from β-alanine was attempted by performing a reaction in the same manner as in Example 1. However, the reaction conditions were altered as shown below.
Altered Reaction Conditions
Reaction temperature: 400° C.
Reaction pressure: 40 MPa
High-temperature high-pressure water density: 0.524 g/cm$^3$ Carrier water flow velocity: 10 ml/min
Substrate solution flow velocity: 2 ml/min The β-alanine concentration prior to introduction into the reaction vessel was 83.3 mM. The reaction time was 0.217 seconds, and when the aqueous solution following the reaction was investigated using a high-performance liquid chromatography mass analysis apparatus, it was confirmed that β-propiolactam had been produced. The concentration of β-propiolactam in the solution was 63.3 mM, and the reaction yield was 76.0%.

EXAMPLE 7

The synthesis of 4-methyl-2-azethidinone from 3-amino-n-butyric acid (reagent chemicals manufactured by Wako Jun'yaku K.K.) was attempted by performing a reaction in the same manner as in Example 1. Distilled water from which solute oxygen had been removed by bubbling with nitrogen gas was used, and a substrate solution with a concentration of 0.100 M was prepared and supplied to the reaction. However, the reaction conditions were altered as shown below.

Altered Reaction Conditions
Reaction temperature: 383° C.
Reaction pressure: 30 MPa
High-temperature high-pressure water density: 0.504 g/cm$^3$
Carrier water flow velocity: 6 ml/min
Substrate solution flow velocity: 4 ml/min The concentration of the 3-amino-n-butyric acid prior to introduction into the reaction vessel was 40 mM. The reaction time was 0.251 seconds, and when the aqueous solution following the reaction was investigated using a high-performance liquid chromatography mass analysis apparatus, it was confirmed that 4-methyl-2-azethidinone had been produced. The content of 4-methyl-2-azethidinone as a β-lactam in the solution was 24.3 mM, and the reaction yield was 60.8%.

EXAMPLE 8

Figure 2:
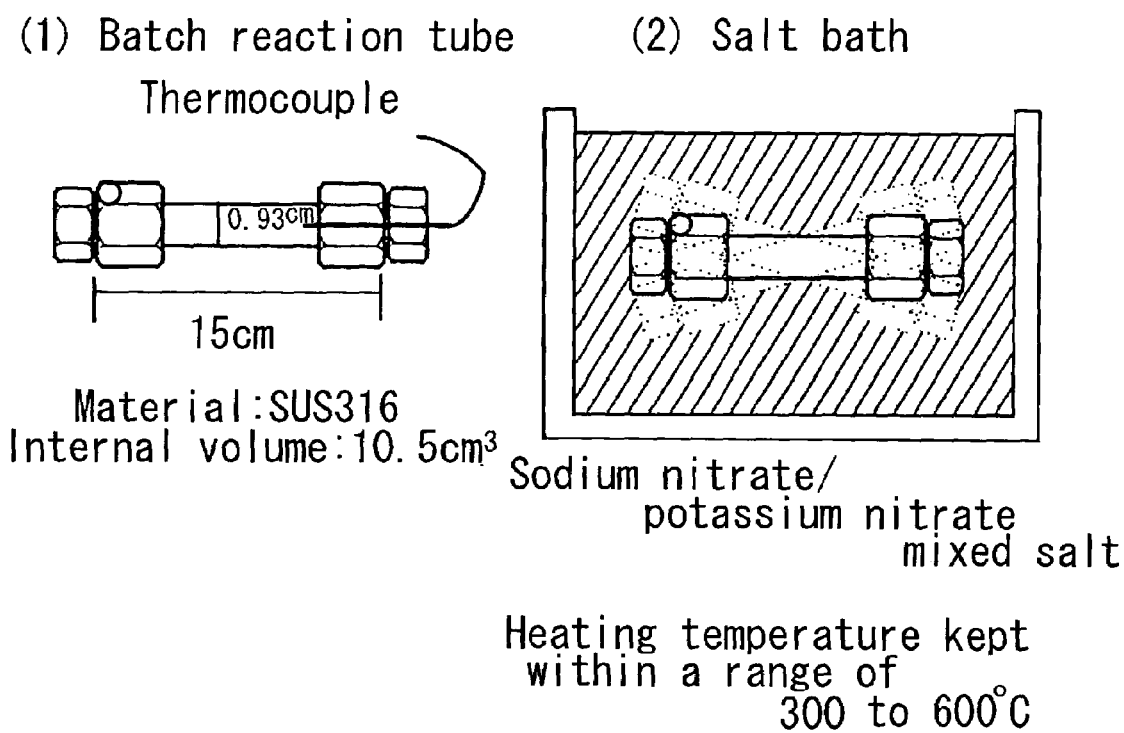
FIG. 2 shows an outline of a batch type reaction tube and an agitation type salt bath tank using a mixed salt of sodium nitrate and potassium nitrate, which are used in a batch type reaction.

The synthesis of β-propiolactam was attempted under high-temperature high-pressure water conditions using β-alanine as a reaction substrate. The reaction was performed using the batch type reaction apparatus shown in FIG. 2, which has shaking and agitation means. A reaction tube with an internal volume of 10.5 cm$^3$ was used as the reaction vessel; this reaction tube was placed in a salt bath tank containing a mixed salt of sodium nitrate and potassium nitrate in which the temperature was 350° C. and the pressure was 30 MPa for 60 seconds, so that an amino group introduction reaction was performed. A time of 40 seconds was required in order to elevate the temperature to the reaction temperature, and the reaction temperature was 20 seconds. The concentration of β-alanine in the reaction solution prior to the reaction was 0.6 M. When the solution obtained following the reaction was investigated using a high-performance liquid chromatography mass analysis apparatus, it was confirmed that β-propiolactam with a concentration of 0.219 M had been produced. The reaction yield of β-propiolactam was 36.5%.

INDUSTRIAL APPLICABILITY

As was described above in detail, the present invention relates to a method for synthesizing β-lactams without using a ring-closing agent by simply reacting β-amino acids under high-temperature high-pressure water conditions. The following exceptional merits are obtained by using the method of the present invention: 1) A method for synthesizing novel β-lactams under high temperature and high pressure can be provided. 2) β-lactams can be synthesized by reacting β-amino acids under high temperature and high pressure. 3) The abovementioned β-lactam synthesis method can be applied to a flow-through system, so that β-lactams can be continuously manufactured from β-amino acids at a high speed. 4) A β-lactam synthesis method which uses absolutely no ring-closing agents, catalysts or organic solvents can be provided. 5) High-purity β-lactams can be manufactured. 6) This chemical substance production system is friendly to the environment.

The invention claimed is:

1. A method for synthesizing a β-lactam comprising reacting a β-amino acid in water in a reaction vessel at high-temperature and under high-pressure conditions for a reaction time of 0.001 seconds to 10 minutes to synthesize the β-lactam;
   wherein the temperature range is 200 ° C. or higher;
   wherein the pressure range is 10 MPa or higher;
   wherein β-lactam is expressed by the formula:

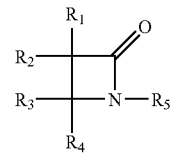

wherein $R_1$, $R_2$, $R_3$, $R_4$ and R5 may be the same or different groups, and respectively indicate hydrogen, halogen, alkyl groups, phenyl groups, phenylalkyl groups, aryl groups, cycloalkyl groups, atkenyl groups, or arylalkyl groups with 1 to 15 carbon atoms, which may be unsubstituted or substituted by substituent groups; and
   wherein the substituent groups are halogen atoms, amido groups, nitro groups, alkoxy groups, acetoxy groups, hydroxyl groups, mercapto groups, phosphoric acid groups, tosyl groups, acyl groups, imido groups, phosphine groups, nitrile groups, or alkylsilyl groups.

2. The method according to claim 1, wherein the β-amino acid is continuously introduced into the reaction vessel.

3. The method according to claim 1 or claim 2, wherein β-propiolactam is synthesized using β-alanine as the β-amino acid.

4. The method according to claim 1 or claim 2, wherein 4-methyl-2-azetidinone is synthesized using 3-amino-n-butyric acid as the β-amino acid.

5. The method of claim 2, wherein the reaction temperature range is 300 ° C. or higher, the pressure range is 15 MPa or greater, and the reaction time is from 0.001 seconds to 5 minutes.

6. A method for manufacturing a β-lactam using a β-amino acid as a reaction substrate under high-temperature high-pressure water conditions, comprising
   introducing a β-amino acid continuously into a reaction vessel under high-temperature high-pressure water conditions in which the temperature range is 200 ° C. or higher, and the pressure range is 10 MPa or greater,
   reacting the β-amino acid for 0.01 seconds to 5 minutes, and
   isolating the β-lactam from the reaction solution.

7. The method of claim 3, wherein the reaction temperature range is 300 ° C. or higher, the pressure range is 15 MPa or greater, and the reaction time is from 0.001 seconds to 5 minutes.

8. The method of claim 4, wherein the reaction temperature range is 300 ° C. or higher, the pressure range is 15 MPa or greater, and the reaction time is from 0.001 seconds to 5 minutes.

9. The method of claim 6, wherein the isolating the β-lactam from the reaction solution comprises
    applying the reaction solution to a column separation medium, and
    collecting the β-lactam.

10. The method of claim 9, wherein the column separation medium comprises an ion exchange resin.

* * * * *